United States Patent [19]
Chappell et al.

[11] Patent Number: 5,968,029
[45] Date of Patent: Oct. 19, 1999

[54] WEB MATERIALS EXHIBITING ELASTIC-LIKE BEHAVIOR

[75] Inventors: Charles W. Chappell, West Chester; John J. Curro, Cincinnati; Michele A. Mansfield, Cincinnati; Richard W. Lodge, Cincinnati, all of Ohio

[73] Assignee: The Procter & Gamble Company, Cincinnati, Ohio

[21] Appl. No.: 09/006,974

[22] Filed: Jan. 14, 1998

Related U.S. Application Data

[63] Continuation-in-part of application No. 08/692,986, Aug. 7, 1996, Pat. No. 5,723,087, which is a continuation of application No. 08/566,203, Dec. 1, 1995, abandoned, and a division of application No. 08/535,798, Sep. 28, 1995, abandoned, which is a division of application No. 08/203,087, Feb. 28, 1994, Pat. No. 5,518,801, which is a continuation-in-part of application No. 08/100,958, Aug. 3, 1993, abandoned.

[51] Int. Cl.$^6$ ............................... A61F 13/15; B32B 3/28
[52] U.S. Cl. ...................... 604/385.1; 604/358; 428/179; 428/181
[58] Field of Search ...................... 604/358, 373, 604/385.1, 387; 428/181, 179

[56] References Cited

U.S. PATENT DOCUMENTS 5,202,173  4/1993  Wu et al. ................................. 428/131

*Primary Examiner*—John G. Weiss
*Assistant Examiner*—Catherine Cogut
*Attorney, Agent, or Firm*—David M. Weirich; Steven W. Miller; Jacobus C. Rasser

[57] ABSTRACT

The present invention is directed to a macroscopically three-dimensional formed substrate including a first boundary zone having a first surface pathlength and a second boundary zone having a second surface pathlength. The first and the second surface pathlengths are preferably measured when the formed substrate is in a relaxed condition. The substrate also includes an elongated zone located at least partially between the first boundary zone and the second boundary zone. The elongated zone comprises incrementally stretched regions which result in the elongated zone being elongated in a first direction of elongation and having a third surface pathlength measured when the formed substrate is in the relaxed condition. The third surface pathlength is greater than either the first pathlength or the second pathlength such that the substrate takes on a macroscopic three-dimensional configuration when the backsheet is in a relaxed condition.

24 Claims, 13 Drawing Sheets

WEB MATERIALS EXHIBITING ELASTIC-LIKE BEHAVIOR

This is a continuation-in-part of application Ser. No. 08/692,986, filed on Aug. 7, 1996 now U.S. Pat. No. 5,723,087, issued on Mar. 3, 1998; which is a continuation of application Ser. No. 08/566,203 filed on Dec. 1, 1995 now abandoned; and is a divisional of application Ser. No. 08/535,798, abandoned, filed Sep. 28, 1995; which is a divisional of application Ser. No. 08/203,087, filed on Feb, 28, 1994 which issued as U.S. Pat. No. 5,518,801 on May 21, 1996; which is a continuation-in-part of application Ser. No. 08/100,958, abandoned, filed on Aug. 3, 1993 now abandoned.

FIELD OF THE INVENTION

The present invention relates to formed substrates capable of assuming a macroscopic three-dimensional configurations, and more particularly, to flexible substrates having three-dimensional configurations that can be useful in both durable and disposable products, including, but not limited to, disposable absorbent articles such as disposable diapers, incontinence garments, training pants, feminine hygiene garments, bandages and the like.

BACKGROUND OF THE INVENTION

Infants and other incontinent individuals wear absorbent articles such as diapers to receive and contain urine and other body exudates. Absorbent articles function both to contain the discharged materials and to isolate these materials from the body of the wearer and from the wearer's garments and bed clothing.

Early prior art disposable diapers were generally flat composite sheets which were fitted to a baby in a flat state or incorporated geometric folding to achieve a suitable "baby shape." A major in-use problem with these prior art diapers is that gaps between the diaper and the baby's body tended to develop due to the semi-rigid nature of the absorbent body, especially after the diaper had been worn for a period of time. The gaps permitted leakage from the disposable diaper, thereby creating damp or wetted outer clothing and bedding around the baby.

One solution to the aforementioned problem is the use of elastics in the leg openings of the diaper to provide improved fit and containment characteristics. An example of such a prior art disposable diaper is disclosed in U.S. Pat. No. 3,860,003 issued to Buell on Jan. 14, 1975. While elasticized diapers such as those disclosed in Buell have achieved widespread acceptance and commercial success, the elasticized diapers still have a tendency to gap and therefore leak periodically.

A disposable diaper which conforms readily to the contours of the wearer's body offers many benefits including comfort, performance, containment and the like. By more readily conforming to the contours of the body the absorbent article employing the semi-elastic material of the present invention will fit more snugly, thereby reducing the likelihood of leakage of body exudates. Further, by conforming to the contours of the body, the absorbent article employing the three-dimensional substrate of the present invention will help reduce red marking of the skin by eliminating the need for excessive tensional forces used to shape the article.

The advantages of a three-dimensional article are provided by the incorporation of one or more formed substrates. Generally, such formed substrates comprise elongated zones which are incrementally stretched so as to increase their surface pathlength and boundary zones with shorter surface pathlengths disposed adjacent the elongated zone. The incrementally stretched elongated zone along with the boundary zones provides the substrate with a three-dimensional configuration without added forces or elastics. Thus, three-dimensional articles, as described herein, can be manufactured more quickly, easily and inexpensively than similar products currently in the market, thereby reducing their overall cost.

Thus, an object of the present invention is to provide an absorbent article comprising a formed substrate capable of assuming a macroscopic three-dimensional configuration.

Another object of the present invention to provide an absorbent article with a topsheet and/or backsheet comprising a formed substrate capable of assuming a macroscopic three-dimensional configuration in a relaxed condition.

Yet another object of the present invention to provide an absorbent article with a topsheet and/or backsheet comprising a formed substrate capable of assuming a macroscopic three-dimensional configuration in a relaxed condition without added elastics.

These and other objects of the present invention will be more readily apparent when considered in reference to the following description and when taken in conjunction with accompanying drawings.

SUMMARY OF THE INVENTION

The present invention is directed to an absorbent article having a pair of opposed longitudinal edges and including an absorbent assembly having an inner facing side and an outer facing side, and a backsheet joined with the outer facing side of the absorbent assembly. The backsheet includes a formed substrate comprising a first boundary zone having a first surface pathlength and a second boundary zone having a second surface pathlength. The first and the second surface pathlengths are preferably measured when the formed substrate is in a relaxed condition. The backsheet also includes an elongated zone located at least partially between the first boundary zone and the second boundary zone. The elongated zone comprises incrementally stretched regions which result in the elongated zone being elongated in a first direction of elongation and having a third surface pathlength measured when the formed substrate is in the relaxed condition. The third surface pathlength is greater than either the first pathlength or the second pathlength such that the backsheet takes on a macroscopic three-dimensional configuration when the backsheet is in a relaxed condition.

BRIEF DESCRIPTION OF THE DRAWINGS

While the specification concludes with claims particularly pointing out and distinctly claiming the present invention, it is believed that the present invention will be better understood from the following description taken in conjunction with the accompanying drawings in which like reference numerals identify like elements.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted, or otherwise disposed of in an environmentally compatible manner). A "unitary" absorbent article refers to absorbent articles which are formed of separate parts united together to form a coordinated entity so that they do not require separate manipulative parts like a separate holder and liner. Because of their single use nature, low cost materials and methods of construction are highly desirable in disposable absorbent articles.

While the present invention will be described in the context of a formed substrate capable of assuming a macroscopic three-dimensional configuration which is suitable for use as a backsheet on a disposable absorbent article such as a disposable diaper, feminine hygiene garment, catamenial pad, incontinence garments, training pants, diaper holders and liners, bandages, and the like, the present invention is in no way limited to such applications. In fact, the present invention may be practiced to great advantage in many situations where it is desired to provide a polymeric film or web exhibiting a macroscopic three-dimensional configuration. Some examples of other uses of the present invention include packaging materials such as blister packs, liners, or lids; shower caps and other personal hygiene articles; bags; pouches; covers; tubes; condoms; belts, filters, etc. The detailed description of one preferred configuration of the present invention and its use as a backsheet on an absorbent article will allow one skilled in the art to readily adapt the present invention to other applications.

Figure 1:
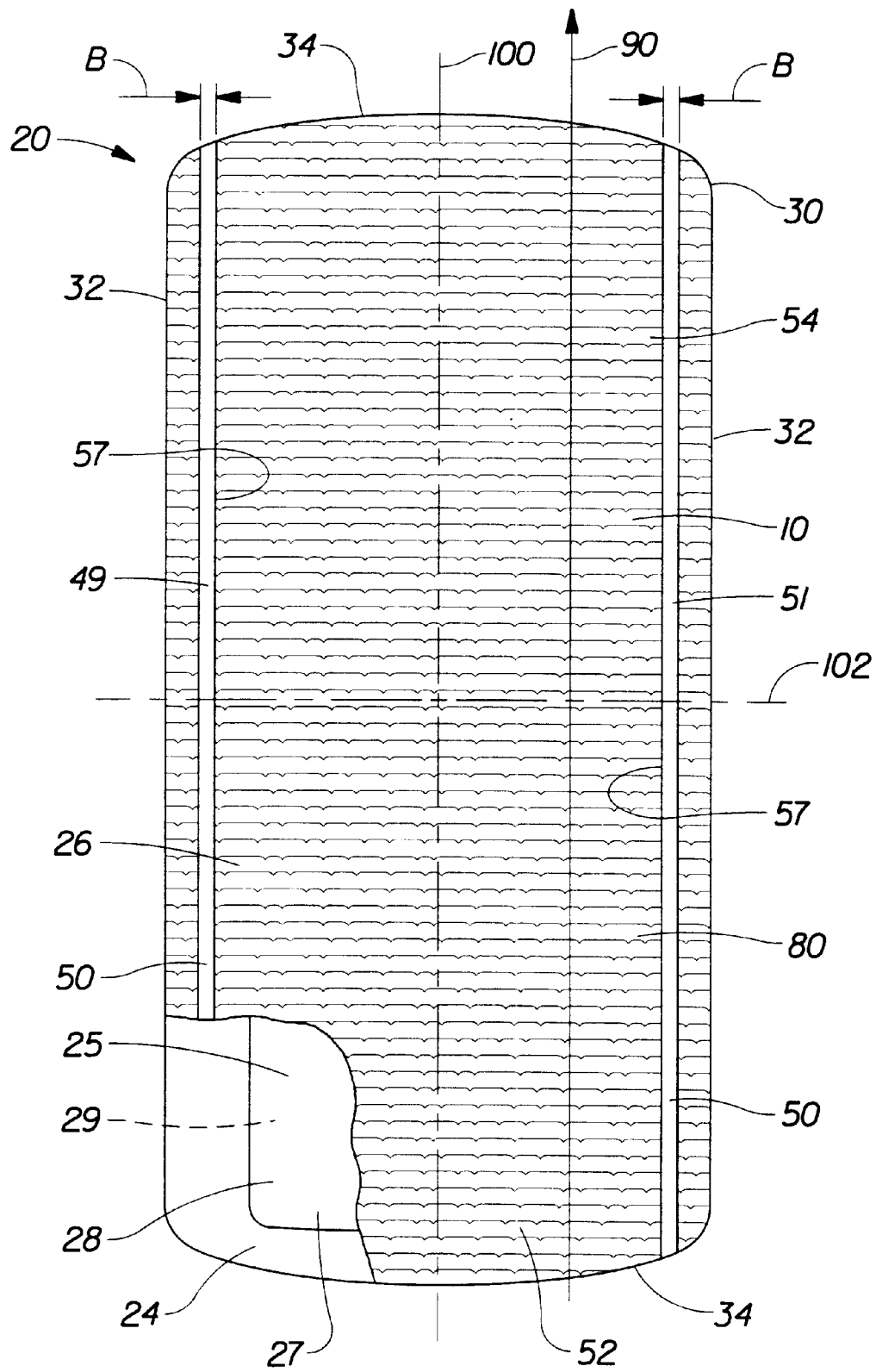
FIG. 1 is a plan view of one embodiment of a sanitary napkin of the present invention having a portion cut-away, with the backsheet facing the viewer, shown in a flat, uncontracted configuration.

A preferred embodiment of a unitary disposable absorbent article of the present invention is the catamenial pad, sanitary napkin 20 shown in FIG. 1. As used herein, the term "sanitary napkin" refers to an absorbent article which is worn by females adjacent to the pudendal region generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. As used herein, the term "pudendal" refers to the externally visible female genitalia.

FIG. 1 is a plan view of a sanitary napkin 20 embodiment of the present invention in its flat out state with portions of the structure being cut-away to more clearly show the construction of the sanitary napkin 20 and with the portion of the sanitary napkin 20 which faces away from the wearer, oriented towards the viewer. As shown in FIG. 1, the sanitary napkin 20 preferably comprises a liquid pervious topsheet 24, a liquid impervious backsheet 26 joined to the topsheet 24, and an absorbent assembly 25 positioned between the topsheet 24 and the backsheet 26.

The sanitary napkin 20 has two surfaces, a body-contacting surface or "body surface" and a garment-facing or "garment surface". The sanitary napkin 20 is shown in FIG. 1 as viewed from its garment surface. The body surface is intended to be worn adjacent to the body of the wearer while the garment surface is on the opposite side and is intended to be placed adjacent the wearer's undergarments when the sanitary napkin 20 is worn.

The sanitary napkin 20 also has two centerlines, a longitudinal centerline 100 and a lateral centerline 102. The term "longitudinal", as used herein, refers to a line, axis, or direction in the plane of the sanitary napkin 20 that is generally aligned with (e.g. approximately parallel with) a vertical plane which bisects the standing wearer into left and right body halves when the sanitary napkin 20 is worn. The terms "lateral" and "transverse" as used herein are interchangeable and refer to a line, axis or direction which lies within the plane of the sanitary napkin that is generally perpendicular to the longitudinal direction (which divides the wearer into front and back body halves). FIG. 1 also shows that the sanitary napkin 20 has a periphery 30 which is defined by the outer edges of the sanitary napkin 20 in which the longitudinal edges are designated 32 and the end edges are designated 34.

In one preferred embodiment of the sanitary napkin 20, the topsheet 24 and the backsheet 26 have length and width dimensions generally larger than those of the absorbent assembly 25. The topsheet 24 and the backsheet 26 may extend beyond the edges of the absorbent assembly 25 to thereby form the periphery 30 of the sanitary napkin 20.

The absorbent article preferably comprises an absorbent assembly 25. In preferred embodiments the absorbent assembly 25 preferably comprises an absorbent core 28. The absorbent assembly 25 may include any absorbent core or any other absorbent member which is capable of absorbing and retaining liquids such as urine and/or menses. The absorbent assembly 25 has an inner facing surface 29, an outer surface 27, side edges, and end edges. The absorbent assembly 25 may be manufactured in a wide variety of sizes and shapes (e.g., rectangular, hour-glass, oval, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulosic wading; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials.

The configuration and construction of the absorbent assembly 25 and/or the absorbent core 28 may vary (e.g., the absorbent core may have varying caliper zones, hydrophilic gradients, superabsorbent gradients, or lower average density and lower average basis weight acquisition zones; or may comprise one or more layers or structures). Further, the size and absorbent capacity of the absorbent assembly 25 may be varied to accommodate different users. However, the total absorbent capacity of the absorbent assembly 25 should be compatible with the design loading and the intended use of the sanitary napkin 20.

Exemplary absorbent structures for use as the absorbent assembly 25 of the present invention are described in U.S. Pat. No. 4,610,678 issued to Weisman et al. on Sep. 9, 1986; U.S. Pat. No. 4,834,735 issued to Alemany et al. on May 30, 1989; U.S. Pat. No. 4,950,264 issued to Osborn on Aug. 21, 1990; and European Patent Application No. 0 198 683, The Procter & Gamble Company, published Oct. 22, 1986 in the name of Duenk, et al. Each of these references is incorporated herein by reference.

The backsheet 26 and the topsheet 24 are preferably positioned adjacent the outer surface 27 and the inner surface 29, respectively, of the absorbent assembly 25 and are preferably joined thereto and to each other by attachment means (not shown) such as those well known in the art. For example, the backsheet 26 and/or the topsheet 24 may be secured to the absorbent assembly 25 or to each other by a uniform continuous layer of adhesive, a patterned layer of adhesive or an array of separate lines, spirals, or spots of adhesive.

Adhesives which have been found to be satisfactory are manufactured by H. B. Fuller Company of St. Paul, Minn. and marketed as HL-1258. An example of a suitable attachment means comprising an opened pattern network of filaments of adhesive is disclosed in U.S. Pat. No. 4,573,986 issued to Minetola et al. on Mar. 4, 1986, and which is incorporated herein by reference. Another suitable attachment means comprising several lines of adhesive filaments swirled into a pattern is illustrated by the apparatus and methods shown in U.S. Pat. No. 3,911,173 issued to Sprague, Jr. on Oct. 7, 1975; U.S. Pat. No. 4,785,996 issued to Ziecker et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably compliant, soft feeling and non-irritating to the wearer's skin. Further, the topsheet 24 is liquid pervious permitting liquids (e.g., menses and/or urine) to readily penetrate through its thickness. Suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. Nos. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel et al. on Aug. 3, 1982; U.S. Pat. No. 4,463,045 issued to Ahr et al. on Jul. 31, 1994; and U.S. Pat. No. 5,006,394 issued to Baird on Apr. 9, 1991. Each of these patents are incorporated herein by reference. The preferred topsheet for the present invention is a formed film described in one or more of the above patents and marketed on sanitary napkins by The Procter & Gamble Company of Cincinnati, Ohio as "DRI-WEAVE".

In a preferred embodiment of the present invention, the body surface of the topsheet 24 is hydrophilic so as to help liquid to transfer through the topsheet 24 faster than if the body surface was not hydrophilic so as to diminish the likelihood that menstrual fluid will flow off the topsheet rather than flowing into and being absorbed by the absorbent assembly 25. In a preferred embodiment where the topsheet is a formed film, surfactant is incorporated into the polymeric materials of the formed film such as is described in U.S. patent application Ser. No. 08/072,660, entitled "Absorbent Article Having a Nonwoven Apertured Film Coversheet" filed on Jun 4, 1993 in the names of Aziz, et al., which is incorporated by reference herein. Alternatively, the body surface of the outer cover may be made hydrophilic by treating it with a surfactant such as described in U.S. Pat. No. 4,950,260, issued to Osborn on Aug. 21, 1990, which is incorporated by reference herein.

The backsheet 26 of the present invention is that portion of the sanitary napkin 20 which is generally positioned away from the wearer's skin and which prevents the exudates absorbed and contained in the absorbent core 28 from wetting articles which contact the sanitary napkin 20 such as bedsheets and undergarments. Thus, the backsheet 26 is preferably impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of article which the materials come in contact with. The backsheet 26 may thus comprise a woven or nonwoven material, polymeric films such as thermoplastic films of polyethylene or polypropylene, composite materials such as a film-coated nonwoven material or materials including one or more apertures or apertured regions. Preferably, the backsheet is a polyethylene or polypropylene film having a thickness of from about 0.012 mm (0.5 mil) to about 0.015 mm (2.0 mil). Exemplary polyethylene films are manufactured by Clopay Corporation of Cincinnati, Ohio under the designation P18-1401 and by Ethyl Corporation, Visqueen Division, of Terre Haute, Indiana, under the designation XP-39385. The backsheet 26 is preferably embossed and/or matte finished to provide a more cloth like appearance. Further, the backsheet 26 may permit vapors to escape from the absorbent assembly 25 (i.e., breathable) while still preventing exudates from passing through the backsheet 26.

The backsheet 26 is preferably positioned adjacent the outer surface 27 of the absorbent assembly 25 and is preferably joined thereto by any suitable attachment means 60 known in the art. For example, the backsheet 26 may be secured to the absorbent assembly 25 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

In a preferred embodiment of the present invention, the backsheet 26 comprises a formed substrate 80. As used herein, the term "formed substrate" refers to a substrate 10 that has been mechanically manipulated so as to provide the substrate 10 with the ability to assume a macroscopic, three-dimensional structure or geometry while in a relaxed state. As used herein, the term "relaxed condition" refers to the condition of a substrate or a portion of a substrate that has no external elongation forces being applied. The formed substrate 80 having a macroscopic three-dimensional configuration has a number of advantages. The formed substrate 80 when used as a backsheet on a disposable absorbent article such as a diaper or sanitary napkin can be made to more readily conform to the contours of the wearer's body via the macroscopic three-dimensional configuration. By more readily conforming to the contours of the wearer's body, the absorbent article employing the formed substrate 80 of the present invention will fit more snugly thereby reducing leakage of body exudates. Furthermore, by conforming to the contours of the wearer's body, the absorbent article employing the substrate of the present invention will reduce red marking of the skin as the absorbent article can be designed to reduce excessive tensional forces.

The Formed Substrate:

FIG. 1 shows one embodiment of the formed substrate 80 of the present invention. The formed substrate 80 is shown in a macroscopically uncontracted configuration; a force has been applied to the formed substrate 80 to extend the substrate such that it is in a macroscopically relatively planar configuration. (As used herein, the term "relatively planar" refers to objects having at least one surface that lies substantially within a single plane.) At least a portion of the formed substrate 80 comprises regions of incremental stretching. As used herein, the terms "incremental stretching" or "incrementally stretched" refer to intermittently mechanically elongated regions of a substrate having a multiplicity of smaller increments which have been individually stretched beyond the plastic yield point of the material to effect permanent elongation.

Any suitable method for providing incrementally stretched regions in the substrate may be used. Some non-limiting preferred methods for providing the incrementally stretched regions are described in detail in U.S. Pat. No. 5,143,679 entitled "Method For Sequentially Stretching Zero Strain Stretch Laminate Web To Impart Elasticity Thereto Without Rupturing The Web" issued to Weber et al. on Sep. 1, 1992, which is hereby incorporated by reference. (Although the Weber et al. patent referenced above a method for sequentially stretching a laminate web, it is recognized that such methods may be used to stretch any suitable web, including single ply and multiple ply webs, films laminates etc.) Alternatively, the formed substrate 80 of the present invention may be provided with incrementally stretched region by methods as described in U.S. Pat. No. 5,518,801 entitled Web Materials Exhibiting Elastic-Like Behavior, which issued to Chappell, et, al. on May 21, 1996, which is also incorporated by reference herein.

Figure 17:
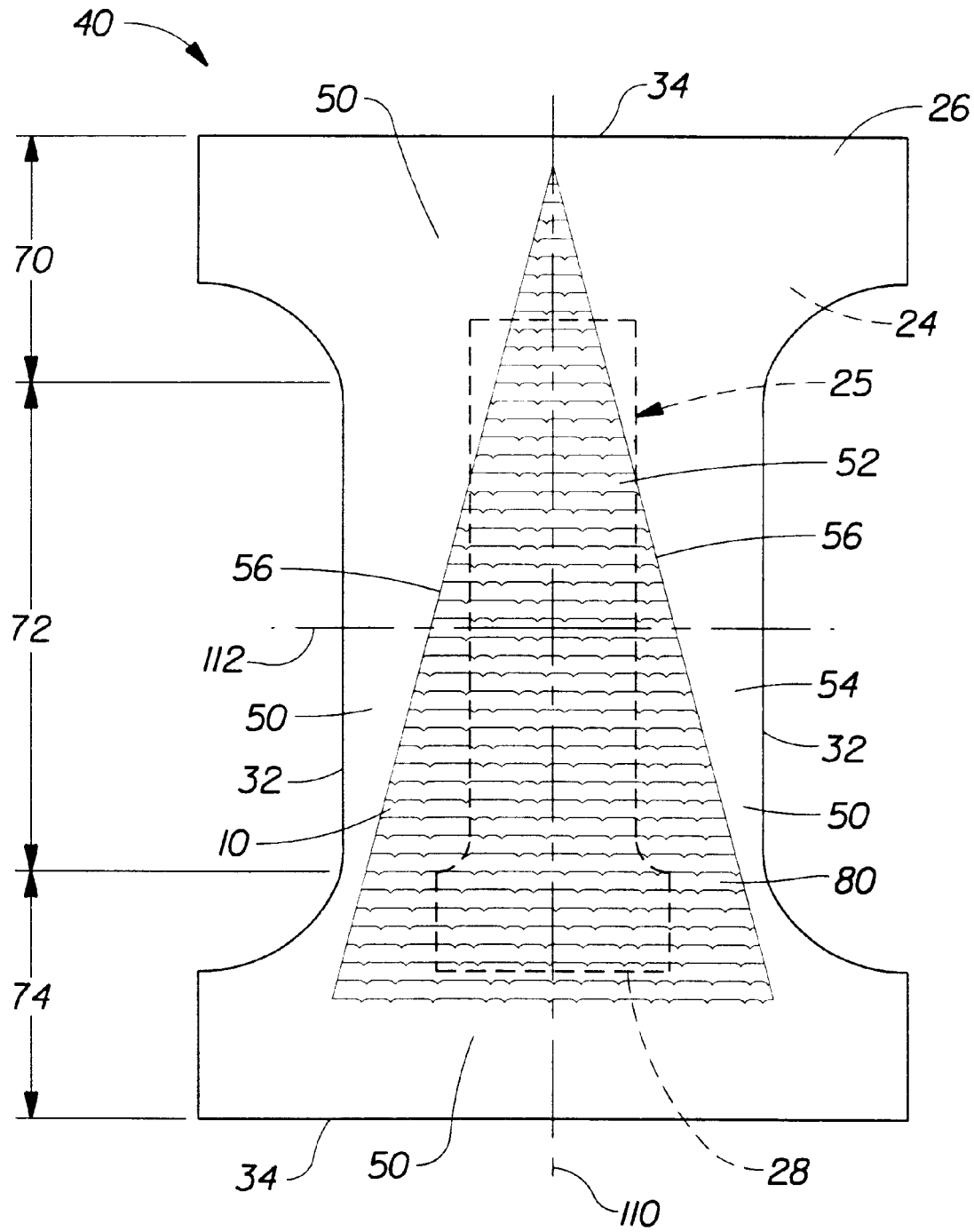
FIG. 17 is a plan view of yet another embodiment of a diaper of the present invention, with the backsheet facing the viewer, shown in a flat, uncontracted configuration.
Figure 18:
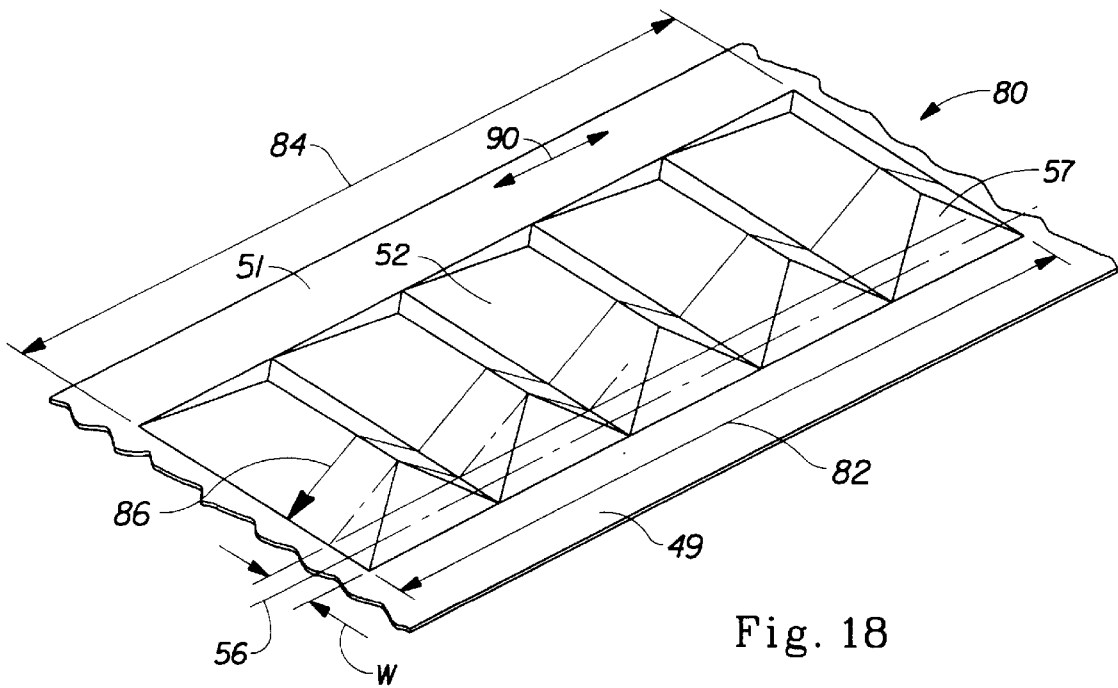
FIG. 18 is a perspective view of a portion of one embodiment of the formed substrate of the present invention.

As shown in FIGS. 1, 4–8 and 11–18, the formed substrate 80 preferably comprises an elongated zone 52, a pair of boundary zones 50, and a transition zone 57 disposed at least partially between the elongated zone 52 and the boundary zone 50. (The transition zone 57 is that portion of the substrate 50 which comprises characteristics of both the elongated zone 52 and the boundary zone 50.) The elongated zone 52 comprises incrementally stretched regions 54 which result in the elongated zone 52 being elongated or extended in a first direction of elongation 90. In one preferred embodiment, the first boundary zone 49 has a first surface pathlength 82, the second boundary zone 51 has a second surface pathlength 84 and the elongated zone 52 has a third surface pathlength 86, examples of which are shown in FIG. 18. (As used herein, the term "surface pathlength" refers to a measurement along the topographic surface of the region or zone in question in a direction generally parallel to an axis. The term "generally parallel" refers to an orientation between axes, elements or a combination of axes and elements whereby the subtended angle formed by the axes or elements being compared is less than 45 degrees. The term "generally perpendicular" refers to an orientation between axes, elements or a combination of axes and elements whereby the subtended angle formed by the axes or elements being compared is greater than 45 degrees.) The surface pathlength of each element is preferably measured as described below.

The elongated zone 52 which is preferably located at least partially between the boundary zones 49 and 51 is incrementally stretched to give it a longer relaxed surface pathlength than the relaxed surface pathlength of either or both of the boundary zones 49 and 51. This difference in pathlengths allows the substrate 80 to take on a three-dimensional shape in a relaxed state without the use of elastics. In some preferred embodiments, it may be desirable to join the formed substrate 80 to another element of the absorbent article which may help maintain the substrate in a three-dimensional configuration. This may help ensure that the formed substrate 80 and thus the absorbent article, is provided in a three-dimensional shape. Otherwise, the article may force the formed substrate into a relatively planar configuration.

It should be noted that the boundary zones 50 may take on any number of shapes, so long as at least a portion of each of the boundary zones 50 is adjacent to at least a portion of elongated zone 52. Thus, the transition zones 57 may be linear (FIGS. 4–6) or curvilinear (FIGS. 7-8), solid (FIGS. 4–8) or intermittent (FIG. 5), or any combination thereof. Further, while the formed substrate 80 may comprise a single, generally regular elongated zone 52, the formed substrate 80 may comprise more than one elongated zone 52. For example, the elongated zones 52 may comprise a series of "bubbles" of incremental stretching interconnected to one another to fit the buttocks of a baby. In addition, the formed substrate 80 may comprise regions of differential incremental stretching or may comprise several different types or directions of incremental stretching in any elongated zone 52. As used herein, the phrase "differential incremental stretching" refers to incremental stretching that provides the particular regions of the substrate with different shape and/or stretch characteristics. (Generally, different regions comprising differential incremental stretching will have different surface pathlengths. However, embodiments are contemplated wherein regions with differential incremental stretching will have the same surface pathlength.) Example of differential incremental stretching would include, but are not limited to regions of the substrate that have been subjected to more than one method of incremental stretching, differing amounts of strain within a region of incremental stretching or differing patterns of incremental stretching within the particular region.

The boundary zone(s) 50 and the elongated zone(s) 52 may comprise the same or different materials. For example, it may be desirable for the boundary zone(s) 50 to be somewhat elastic and the elongated zone(s) 52 to be substantially inelastic. Other different characteristics may also be desirable such as those that relate to stiffness, softness, texture, absorbency, permeability, strength, color or aesthetic qualities, etc. One approach to provide different characteristics in different zones may be to choose a substrate having differing properties within the substrate provided by chemical, mechanical or other means. In one preferred embodiment, at least a portion of the boundary zone(s) 52 may be ring-rolled or incrementally stretched as described below.

The boundary zones 49 and 51 are separated from the elongated zone 52 by a transition zone 57. Within the transition zone 57, the surface topography of the formed substrate 80 transitions to accommodate the change from the surface pathlength in the boundary zones 50 to the elongated pathlength of the elongated zone 52. The width of the transition zone 57 may vary. Generally, the wider the transition zone 57, the more gentle the transition between the boundary zones 50 and the elongated zone 52. The transition between the boundary zone 50 and elongated zone 52 is usually visually apparent by a change in surface appearance, but identification may require microscopic study. A border line 56 is established generally in the center of the transition zone, for the purposes of determining which direction to measure surface pathlength. One example of a border line 56 is shown in FIG. 18.

FIG. 18 is an enlarged perspective view of a portion of one embodiment of a portion of a formed substrate 80 of the present invention in which the topologically flat, unaltered surface of the boundary zone 50 transitions to the rippled or pleated incrementally stretched surface in the elongated zone 52. The transition occurs over a surface consisting of the triangular ends which must exist in order for the surface to be continuous. One skilled in the art will recognize that other geometries could arise depending on the nature of the method used for incrementally stretching the elongated zone 52.

The boundary zones 50 may comprise an unaltered substrate, or may comprise incrementally stretched regions. However, the boundary zone 50 should have a surface pathlength which is shorter than the surface pathlength of the elongated zone 52. Further, the boundary zones 50 may also be gathered by application of a stretched elastic or other means or may itself have elastic, semi-elastic, or plastic stretch characteristics. Alternately the boundary zone 50 may comprise a structural elastic-like film material, as described herein.

Measuring Surface Pathlength:

"Surface pathlength" or "pathlength" is defined as a length of a substrate or any portion thereof measured on the surface of the formed substrate 80 generally parallel to the border 56, as shown in FIG. 18, between the elongated zone 52 and the boundary zone when the portion of the formed substrate 80 is measured in an untensioned state. The surface pathlength is equivalent to the straight line spatial distance between opposite ends of the portion of the formed substrate when the substrate is pulled flat, without generating any tension in the formed substrate 80, eliminating geometric folds, bends, wrinkles, or other "out of plane" structures. If the substrate is very flexible, as is common for the substrate materials typically used in absorbent articles, it can normally be stretched into a substantially flat condition without significant tension. However, it should be recognized by those skilled in the art that if the geometric folds, bends, wrinkles, or other "out of plane" structures are sufficiently stiff so as to require tension in the substrate to flatten them, surface pathlength must be measured by other known means. One example of measuring surface pathlength without pulling the substrate flat is described in U.S. Pat. No. 5,518,801 entitled Web Materials Exhibiting Elastic-Like Behavior, which issued to Chappell, et, al. on May 21, 1996, which is hereby incorporated herein by reference.

For simple geometries such as that shown in FIGS. 1 and 11–14 where the boundary zones are straight and parallel to each other, and the elongated zone 52 is generally uniformly elongated in one direction parallel to the border line 56, surface pathlength can be measured relatively easily. The boundary zone 50 and the adjacent elongated zone 52 are cut apart generally along the border line 56 dividing the two zones. Each zone is then extended to be as flat as possible without inducing tension. The length of each piece is then measured along the border line 56. The elongated zone 52 should be cut to exclude the transition zone 57 located between the boundary zone(s) 50 and the elongated zone 52. If the transition zone 57 is left attached to the elongation zone 52 the transition zone 57 may cause problems properly measuring the surface pathlength of the elongated zone 52 and/or the boundary zone(s) 50.

For more complicated geometries, procedures should be used to take into account the effect of the geometry. Instead of measuring the pathlength of the elongated zone 52 as a whole, it may be easier to get a proper measurement if the formed substrate 80 is cut into narrow strips that are parallel to the boundary zone 50. For example, in cases involving boundary zone(s) 50 with curved edges, the curved border line 56 between the elongated zone 52 and boundary zone(s) 50 may be divided into segments which can be reasonably approximated by straight lines. The segments are marked in both the boundary zone 50 and the elongated zone 52 by lines drawn perpendicular to the border line 56. A sum of the pathlengths measured is determined for each zone (i.e. the sum of the pathlengths of all the segments measured generally equidistant from the border). In the case of curvilinear or irregularly shaped elements, it may be more convenient to use a linear axis which represents an average of the curvilinear element.

While the test method described above is useful for many of the substrates of the present invention it is recognized that the test method may have to be modified to accommodate some of the more complex substrate materials within the scope of the present invention.

Method of Making the Formed Substrate:

Preferred methods of forming the formed substrate(s) 80 of the present invention include, but are not limited to embossing by mating plates or rolls, thermoforming, high pressure hydraulic forming, or casting.

Figure 10:
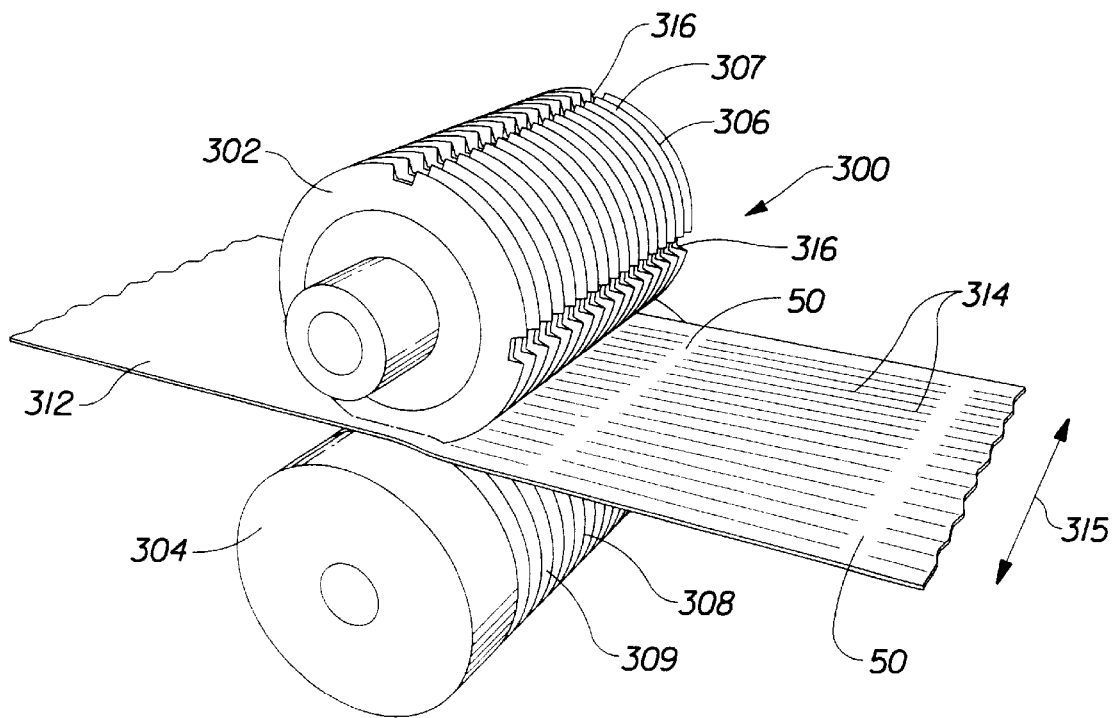
FIG. 10 is another embodiment of an incremental stretching system that can be used to form the incremental stretching regions of the present invention.

Preferably, an incremental stretching system is employed in elongating the elongated zone 52 of the present invention. One preferred incremental stretching system 300 is shown in FIG. 10. Incremental stretching system 300 preferably includes a pair of intermeshing incremental stretching rollers 302 and 304. Roller 302 includes a plurality of teeth 306 and corresponding grooves 307 which are interrupted by zones of no teeth 316 which create the boundary zones 50. Roller 304 includes a plurality of teeth 308 and corresponding grooves 309 which extend about the entire circumferences of roller 304. The teeth 306 on roller 302 intermesh with or engage grooves 309 on roller 304, while the teeth 308 on roller 309 intermesh with or engage grooves 307 on roller 302. As a web, such as web 312 is passed between incremental stretching rollers 302 and 304, web 312 is stretched and/or elongated producing incrementally stretched regions 314 causing the web 312 to be elongated in the cross-machine direction indicated generally by arrows 315. The portion of the web 312 passing between the smooth portions 316 of the roller 302 and the roller 304 will be generally unstrained and thus, will become boundary zones 50. The exact configuration, spacing, dimensions, and overlap of opposing teeth and grooves and rollers 302 and 304 can be adjusted, as desired, to produce the desired results.

Figure 9:
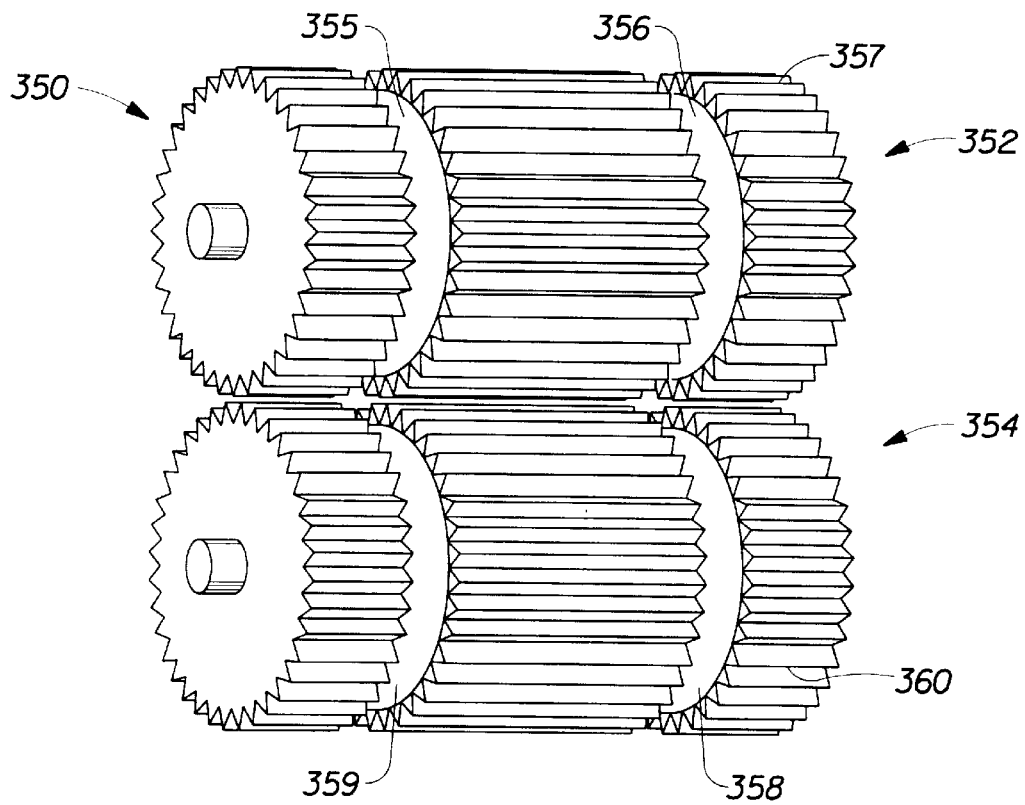
FIG. 9 is one embodiment of an incremental stretching system that can be used to form the incremental stretching regions of the present invention.

Referring now to FIG. 9 there is shown another incremental stretching system 350. Incremental stretching system 350 includes a pair of intermeshing rollers 352 and 354. Roller 352 includes smooth or grooved portions 355 and 356 spaced on either side of a tooth portion 357. Similarly, roller 354 includes a pair of smooth or grooved portions 358 and 359 spaced on either side of a tooth portion 360. Tooth portions 357 and 360 respectively preferably extend about the entire circumference of rolls 302 and 304. Thus, a web material passing between roll 352 and 354 is strained in a discrete portions corresponding to portions 307 and 310 which intermesh with one another to create strained and unstrained areas in the material passing between rollers 352 and 354. This results in at least those portions of the web being subjected to the incremental stretching being elongated in at least the machine direction. The portions of the material passing between smooth portions 355 and 359, and smooth portions 356 and 358, respectively, will be generally unstrained and will remain in generally its precursor condition unless otherwise processed. The material which has been subjected to processing in rollers 352 and 354 will have two boundary zones 50 spaced apart by the elongated zone 52 having strained and unstrained areas, resembling the formed substrate 80 as shown in FIG. 1.

Yet another suitable embodiment of a suitable incremental stretching method which may be employed in making the intermediate elongated zone/s of the present invention are set forth in U.S. Pat. No. 5,143,679 entitled "Method For Sequentially Stretching Zero Strain Stretch Laminate Web To Impart Elasticity Thereto Without Rupturing The Web" issued to Weber et al. on Sep. 1, 1992, and U.S. Pat. No. 5,518,801 entitled Web Materials Exhibiting Elastic-Like Behavior, which issued to Chappell, et, al. on May 21, 1996, each of which is incorporated by reference herein.

The choice of incremental stretch method and width and geometry of the transition zone may reflect aesthetic choices, susceptibility of materials to abrupt changes in pathlength, compatibility with the process used to make the substrate, and other factors recognized by those familiar with the art. Further, depending on the characteristics of the material comprised in the substrate, the formed substrate 80 may be rigid enough to retain the desired structure or geometry when it is not subjected to any externally applied force. Alternatively, the formed substrate 80 may lack the rigidity needed to obtain or retain the desired structure or geometry without an external force. In embodiments such as the sanitary napkin 20 shown in FIGS. 1–3, another element of the article such as the absorbent core 28, a film or a laminate bonded to the formed substrate 80 or an adhesive, such as adhesive 60, joining an element of the sanitary napkin 20 to the formed substrate 80 may provide the formed substrate 80 with the external force necessary for the formed substrate 80 to obtain and maintain a desired macroscopic, three-dimensional structure or geometry.

Although the incremental stretching is described above as generally elongating the formed substrate 80 in either the machine direction or the cross-machine direction, it is contemplated that any portion of the elongated zone(s) 52, or any other portion of the formed substrate 80 may be subjected to incremental stretching which elongates the formed substrate 80 or any portion thereof in directions other than the machine direction or the cross-machine direction. For example, the incremental stretching may elongate the substrate, or any portion thereof, at any angle to the machine or cross-machine direction. (The direction of elongation in complex patterns such as those shown in FIGS. 5–8 may vary throughout the substrate.) Also, embodiments are contemplated wherein the substrate, or portions thereof have been incrementally stretched so as to provide elongation in more than one direction.

Figure 2:
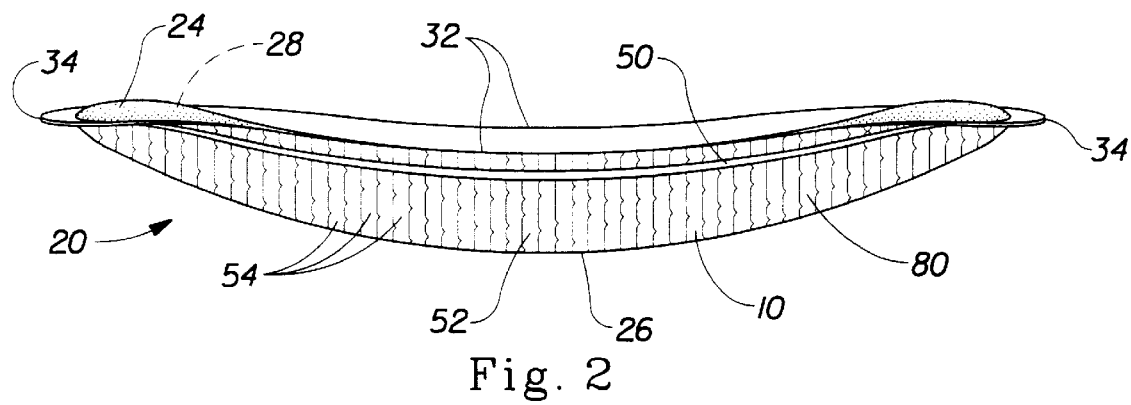
FIG. 2 is a perspective view of the sanitary napkin of FIG. 1 showing the formed substrate in a macroscopic three-dimensional configuration.
Figure 2A:
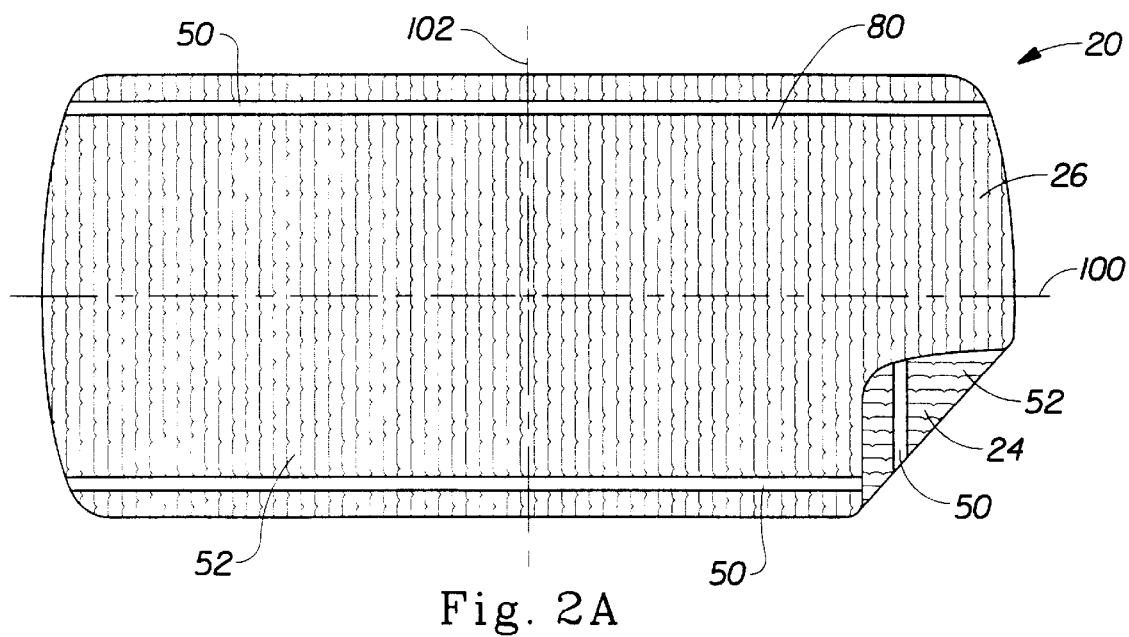
FIG. 2A is a plan view of one embodiment of the present invention.
Figure 3:
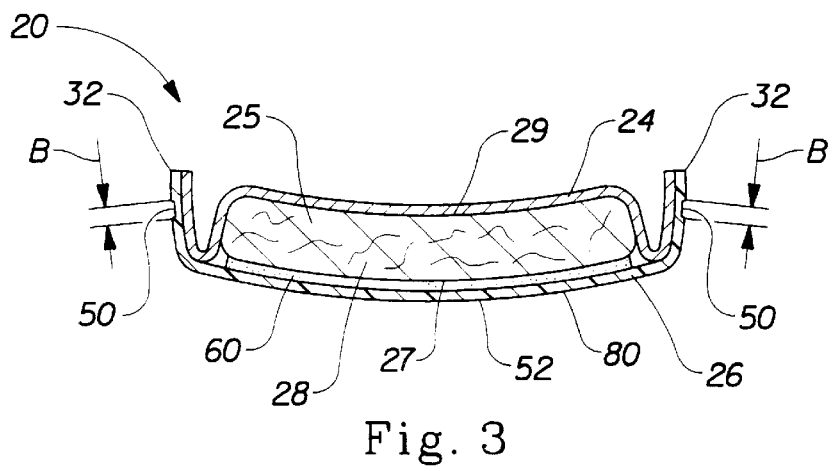
FIG. 3 is a cross-sectional view of the sanitary napkin of FIG. 2.
Figure 4:
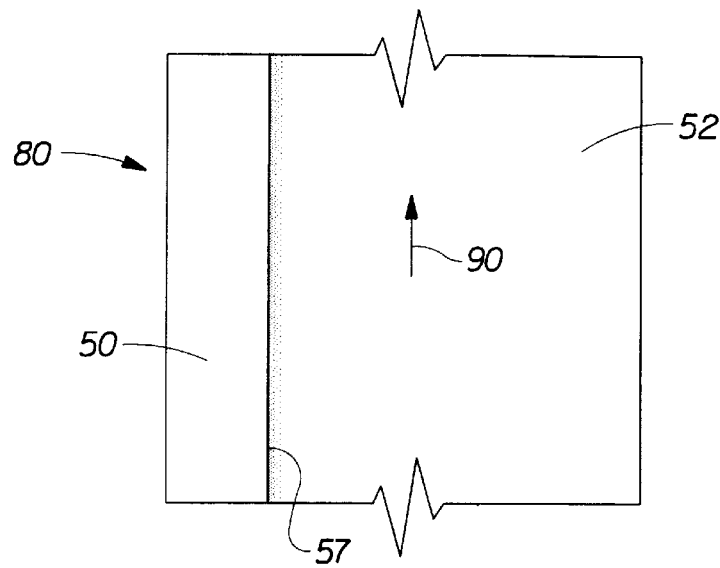
FIG. 4 is a fragmented plan view of one embodiment of the formed substrate of the present invention shown in a relaxed configuration.
Figure 5:
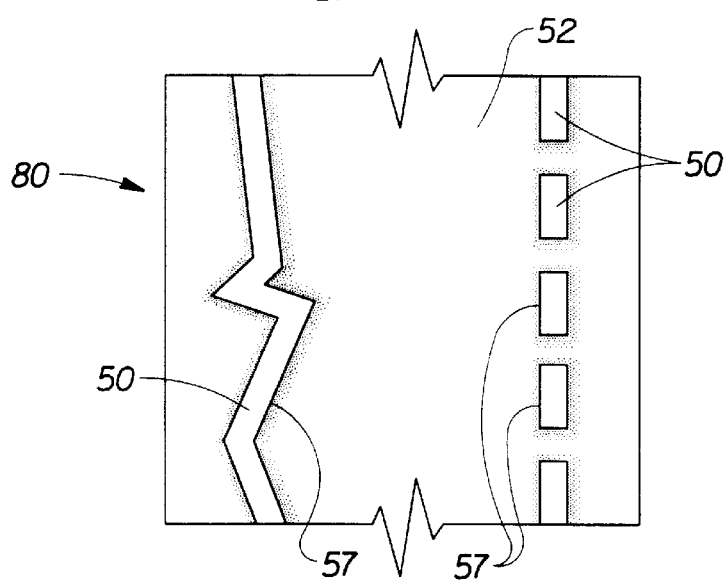
FIG. 5 is a fragmented plan view of an alternative embodiment of the formed substrate of the present invention shown in a relaxed configuration.
Figure 6:
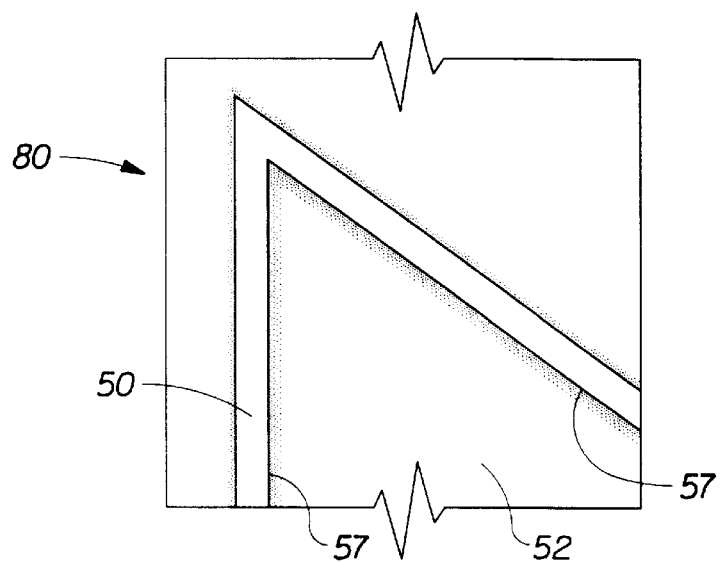
FIG. 6 is a fragmented plan view of another embodiment of the formed substrate of the present invention shown in a relaxed configuration.
Figure 7:
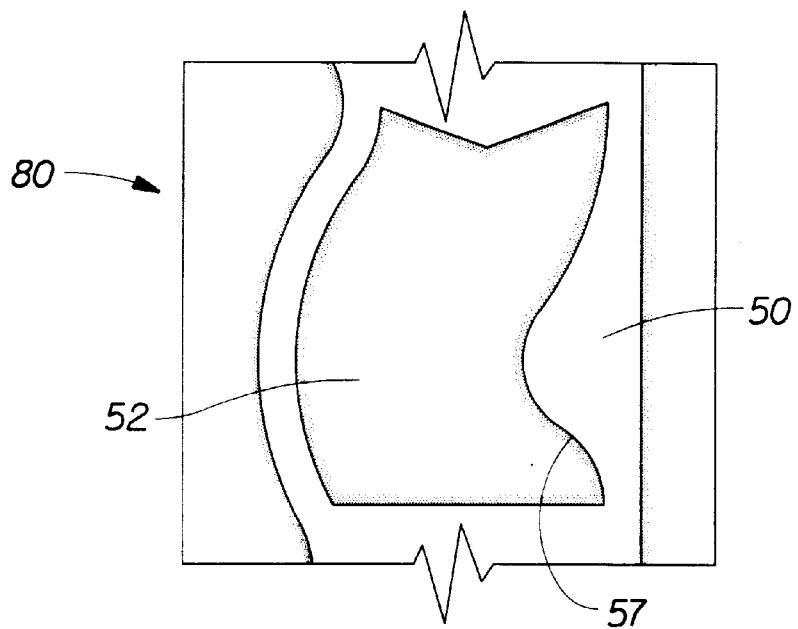
FIG. 7 is a fragmented plan view of another alternative embodiment of the formed substrate of the present invention shown in a relaxed configuration.
Figure 8:
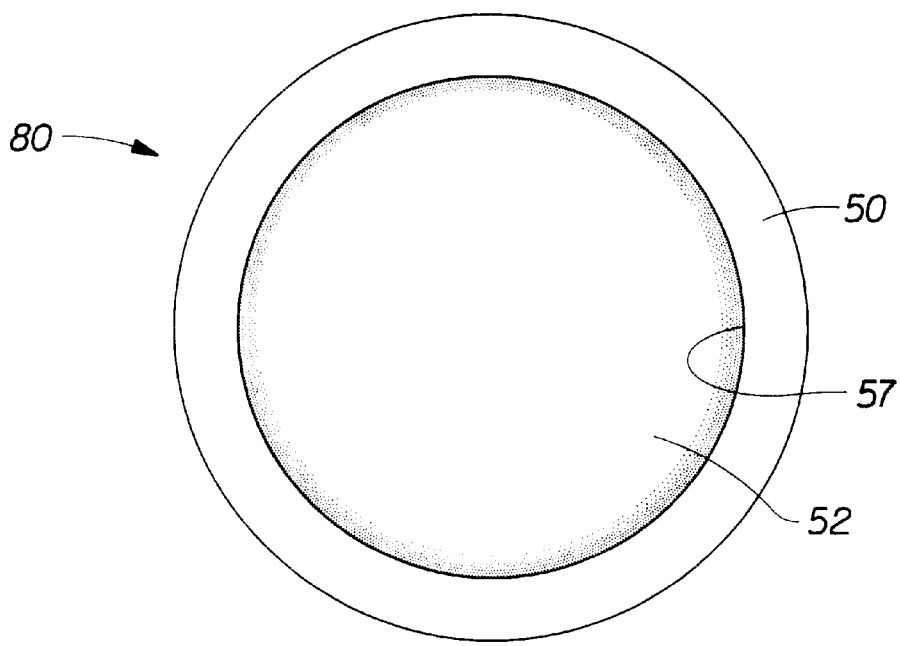
FIG. 8 is a fragmented plan view of yet another alternative embodiment of the formed substrate of the present invention shown in a relaxed configuration.

Preferred Embodiments:

The sanitary napkin 20 shown in FIGS. 1–3 preferably comprises the formed substrate 80 of the present invention. Although the formed substrate 80 could be any of a number of elements comprised in the sanitary napkin 20, one preferred embodiment, as described above, comprises the formed substrate 80 of the present invention as the backsheet 26. In the embodiment shown, the formed substrate 80 comprises an elongated zone 52, at least two boundary zones 50 and a transition zone 57 disposed between each of the boundary zones 50 and the elongated zone 52. In a preferred embodiment, the elongated zone 52 comprises incremental stretched regions 54 that elongate the elongated zone 52 in a direction generally parallel to the longitudinal axis 100 of the sanitary napkin 20. It is also preferred that the transition zones 57 extend in a direction generally parallel to the longitudinal axis 100 as well. In an especially preferred embodiment, the boundary zones 50 are generally parallel to each other and spaced apart by at least a portion of the elongated zone 52.

A preferred sanitary napkin 20 has a pair of opposed longitudinal edges 32 and includes a topsheet 24, a backsheet 26 joined with the topsheet 24 and an absorbent assembly 25 positioned between the topsheet 24 and the backsheet 26. The absorbent assembly 25 preferably has an inner facing side 29 and an outer facing side 27. The topsheet 24 is preferably positioned adjacent the inner facing side 29 of the absorbent assembly 25 and the backsheet 26 is preferably positioned adjacent the outer facing side 27 of the absorbent assembly 25.

As shown in FIGS. 1–3, the backsheet 26 preferably comprises a formed substrate 80 including an elongated zone 52, and two boundary zones 50, a first boundary zone 49 and a second boundary zone 51 extending generally parallel to each of the longitudinal edges 32. Preferably, each boundary zone 50 has a width B between about 0.1 cm and about 3.0 cm. More preferably, the width B of the boundary zones 50 is between about 0.2 cm and about 1.5 cm. It is also preferred that the boundary zones 50 be spaced apart between about 1.0 cm and about 30.0 cm. More preferably, the boundary zones 50 are spaced apart between about 2.0 cm and about 15.0 cm. Even more preferably, the boundary zones 50 are spaced apart between about 4.0 cm and about 10.0 cm. Further is has been found that the spacing of the boundary zones 50 from the longitudinal edges 32 of the sanitary napkin 20 may influence in characteristics of the article. Thus, it has been found that a preferred spacing of the boundary zones 50 from the longitudinal edges 32 of the sanitary napkin 20 is between about 0 mm and about 50 mm, more preferably between about 1 mm and about 30 mm, and most preferably between about 2 mm and about 5 mm.

A transition zone 57 is preferably disposed between the elongated zone 52 and each of the boundary zones 50. The elongated zone 52 preferably comprises incrementally stretched regions 54 which result in the elongated zone 52 being elongated in a first direction of elongation 90. It is also preferred that the first boundary zone 49 have a first surface pathlength 82, the second boundary zone 51 have a second surface pathlength 84 and the elongated zone 52 have a third surface pathlength 86, as shown in FIG. 18. The first surface pathlength 82 and/or the second surface pathlength 84 is less than the third surface pathlength 86 of the elongated zone 52, when the formed substrate 80 is in a relaxed condition. In preferred embodiments, the elongated zone 52 may have a third surface pathlength 86 which is between about 5% and about 500% greater than the first and second surface pathlengths 82 and 84 of the boundary zones 50. More preferably, the surface pathlength of the elongated zone 52 is between about 10% and about 250% greater than the surface pathlength of the boundary zones 50, and most preferably the surface pathlength of the elongated zone 52 is between about 20% and about 100% greater than that the surface pathlength of the boundary zones 50. This ensures that the elongated zone 52 in conjunction with the boundary zones 50 provide the backsheet 26 with a macroscopic three-dimensional configuration when the substrate is in a generally relaxed configuration.

Alternative embodiments of preferred absorbent articles may comprise two or more formed substrates. In one embodiment the topsheet 24 may comprise a formed substrate such as formed substrate 80. Further, any of the formed substrate(s) may comprises regions of differential extensibility, as described herein.

FIGS. 11–17 are plan views of alternative diaper embodiments of the present invention in their flat-out, uncontracted state (i.e., with elastic induced contraction pulled out) with the portion of the diapers 40 which faces away from the wearer oriented towards the viewer. (As used herein, the term "diaper" refers to absorbent articles generally worn by infants to absorb and contain bodily exudates. However, the such absorbent articles are not limited to those articles worn by infants and may include adult incontinence products, training pants, menstrual panties and the like.) The diapers 40 preferably comprises a liquid pervious topsheet 24; a liquid impervious backsheet 26 joined with the topsheet 24 and an absorbent core 28 positioned between the topsheet 24 and the backsheet 26. Each diaper 40 preferably has a front waist region 70, a rear waist region 74 and a crotch region 72 extending between the front waist region 70 and the rear waist region 74. Further, the diaper 40 preferably has longitudinal side edges 32 and end edges 34.

FIGS. 11–17 show preferred embodiments of the diapers 40 in which the topsheet 24 and the backsheet 26 may have length and width dimensions generally larger than those of the absorbent assembly 25. The topsheet 24, the backsheet 26, and the absorbent assembly may be assembled in a variety of well known configurations, and the diapers 40 may comprise other elements such as elasticized side panels; elasticized leg cuffs; elastic waist feature(s), fastening systems as well as other features well known in the art. Exemplary preferred disposable diaper configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092, entitled "Absorbent Article With Dynamic Elastic Waist Feature Having A Predisposed Resilient Flexural Hinge", issued to Kenneth B. Buell et al. on Sep. 29, 1992 which is incorporated herein by reference. Exemplary fastening systems are described in U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; U.S. Pat. No. 3,848,594 issued to Buell on Nov. 19, 1974; U.S. Pat. No. B1 4,662,875 issued to Hirotsu et al. on May 5, 1987, each of which is incorporated herein by reference.

Figure 11:
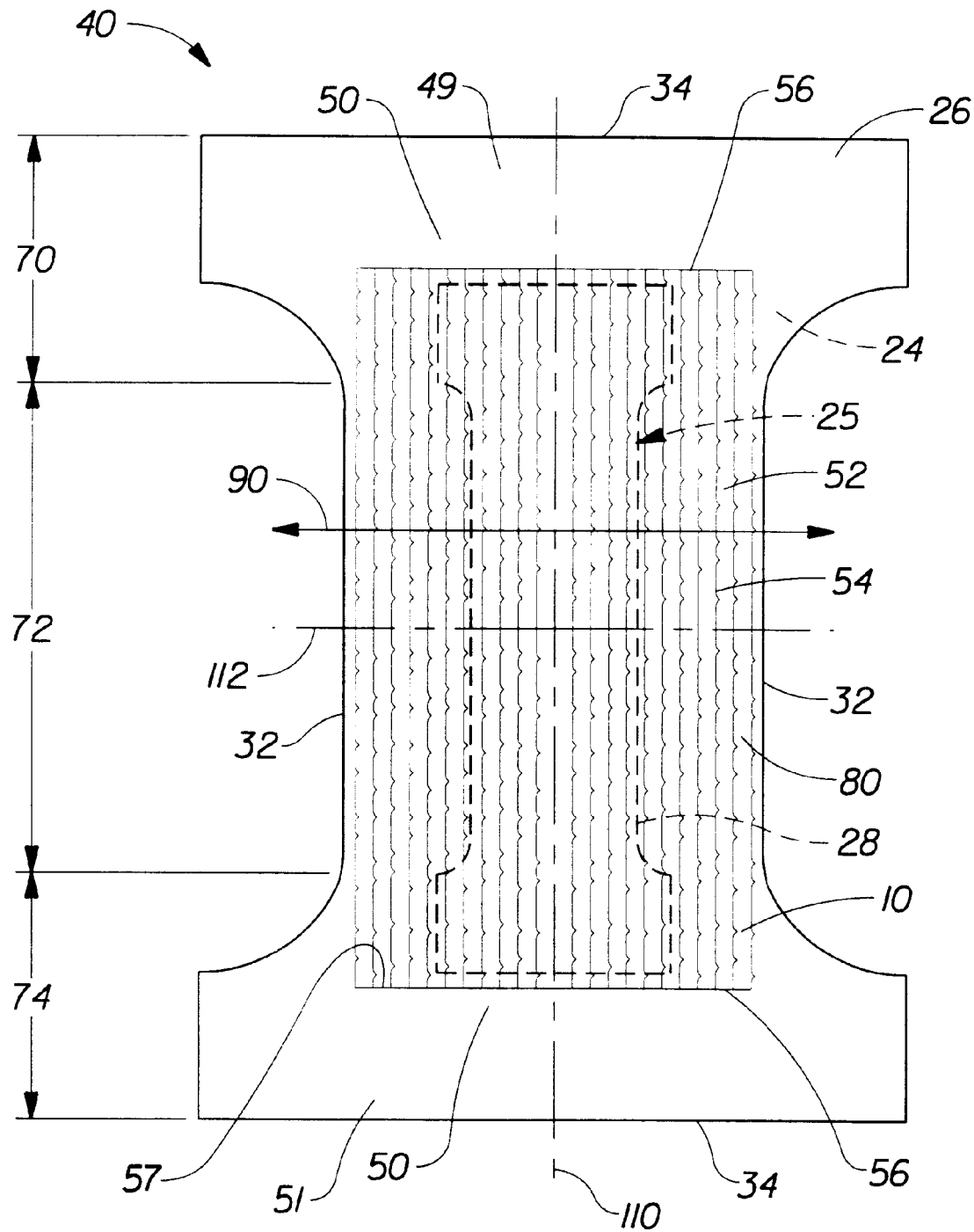
FIG. 11 is a plan view of one embodiment of a diaper of the present invention, with the backsheet facing the viewer, shown in a flat, uncontracted configuration.
Figure 12:
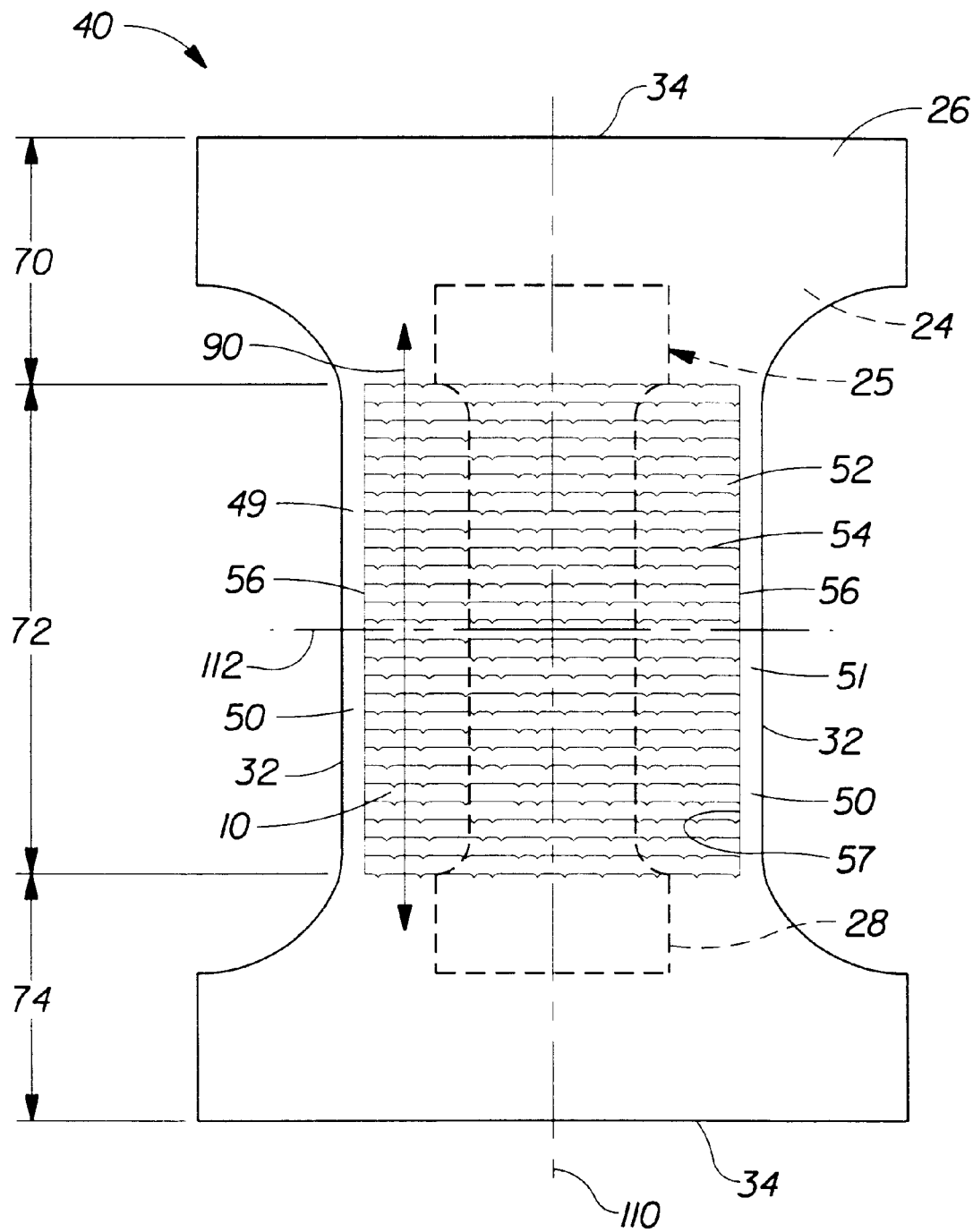
FIG. 12 is a plan view of another embodiment of a diaper of the present invention, with the backsheet facing the viewer, shown in a flat, uncontracted configuration.
Figure 13:
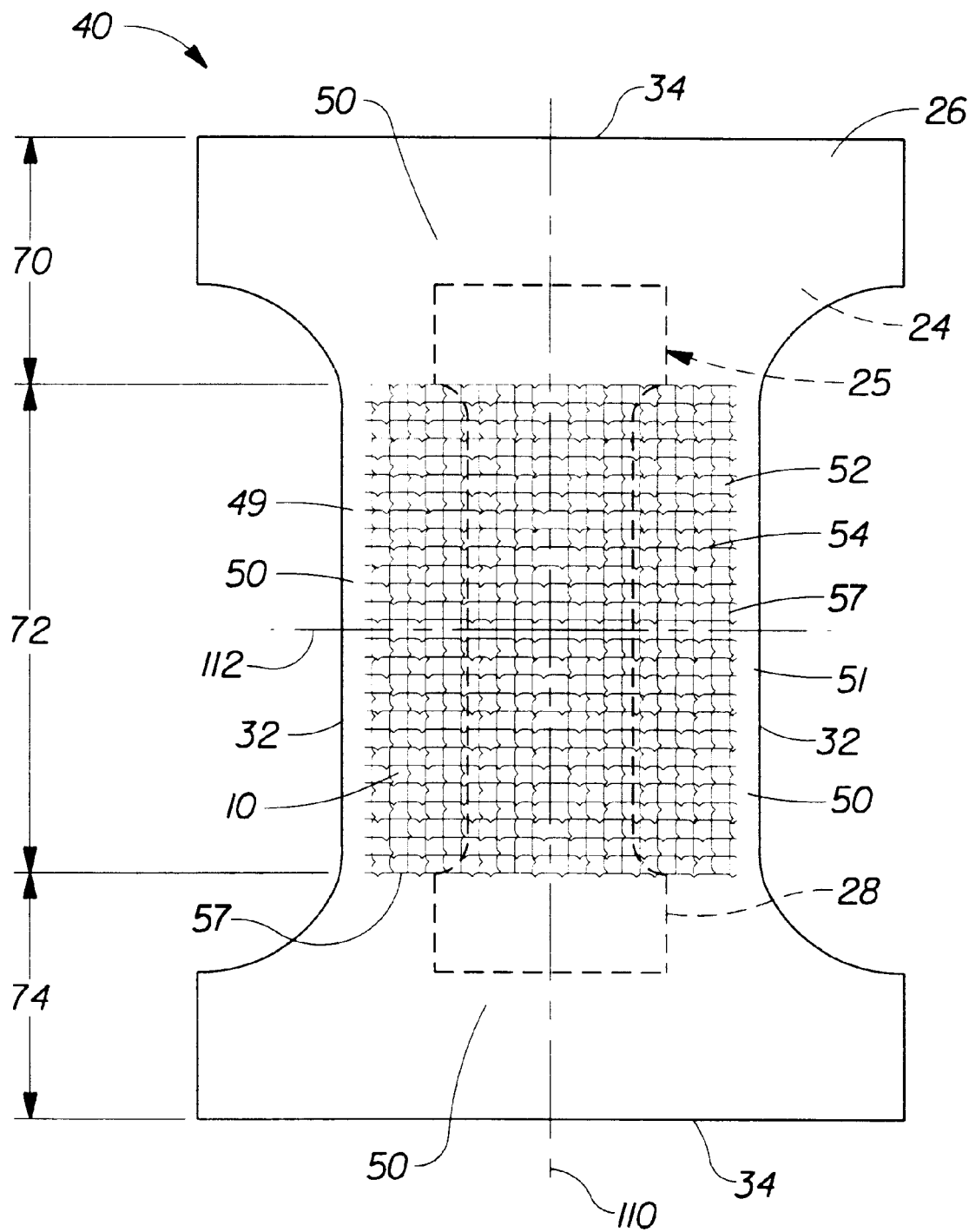
FIG. 13 is a plan view of yet another embodiment of a diaper of the present invention, with the backsheet facing the viewer, shown in a flat, uncontracted configuration.

As shown in FIGS. 11–17, each diaper 40 preferably comprises at least one formed substrate 80. In the embodiment shown, the formed substrate 80 is comprised in the backsheet 26, however, other embodiments are contemplated wherein the formed substrate 80 is comprised in an any number of other elements in the diaper 40. In the embodiments shown, the formed substrate 80 comprises an elongated zone 52, at least two boundary zones 50 and a transition zone 57 disposed between each of the boundary zones 50 and the elongated zone 52. The elongated zone 52 may be elongated in at least a direction generally parallel to the lateral axis 112 of the diaper 40, as shown in FIG. 11, in at least a direction generally parallel to the longitudinal axis 110, as shown in FIG. 12, or in more than one direction, as shown in FIG. 13. The transition zone 57 preferably extends in a direction generally parallel to the direction in which the elongated zones 52 are extended. In especially preferred embodiments, as shown in FIGS. 11–14, the diaper 40 has at least two boundary zones 50, a first boundary zone 49 and a second boundary zone 51. The first and second boundary zones are preferably generally parallel to each other and spaced apart by at least a portion of the elongated zone 52.

Figure 14:
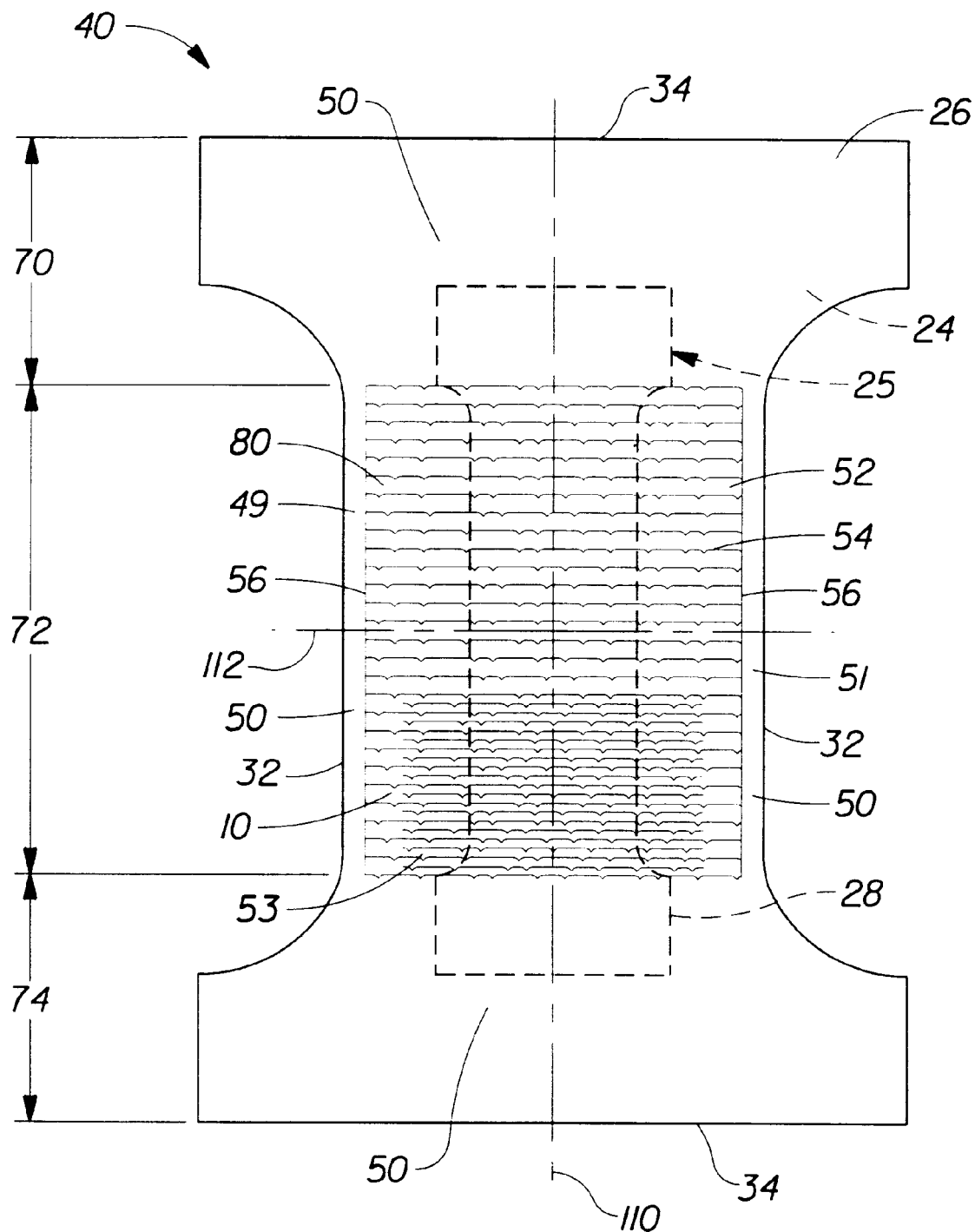
FIG. 14 is a plan view of yet another embodiment of a diaper of the present invention, with the backsheet facing the viewer, shown in a flat, uncontracted configuration.
Figure 15:
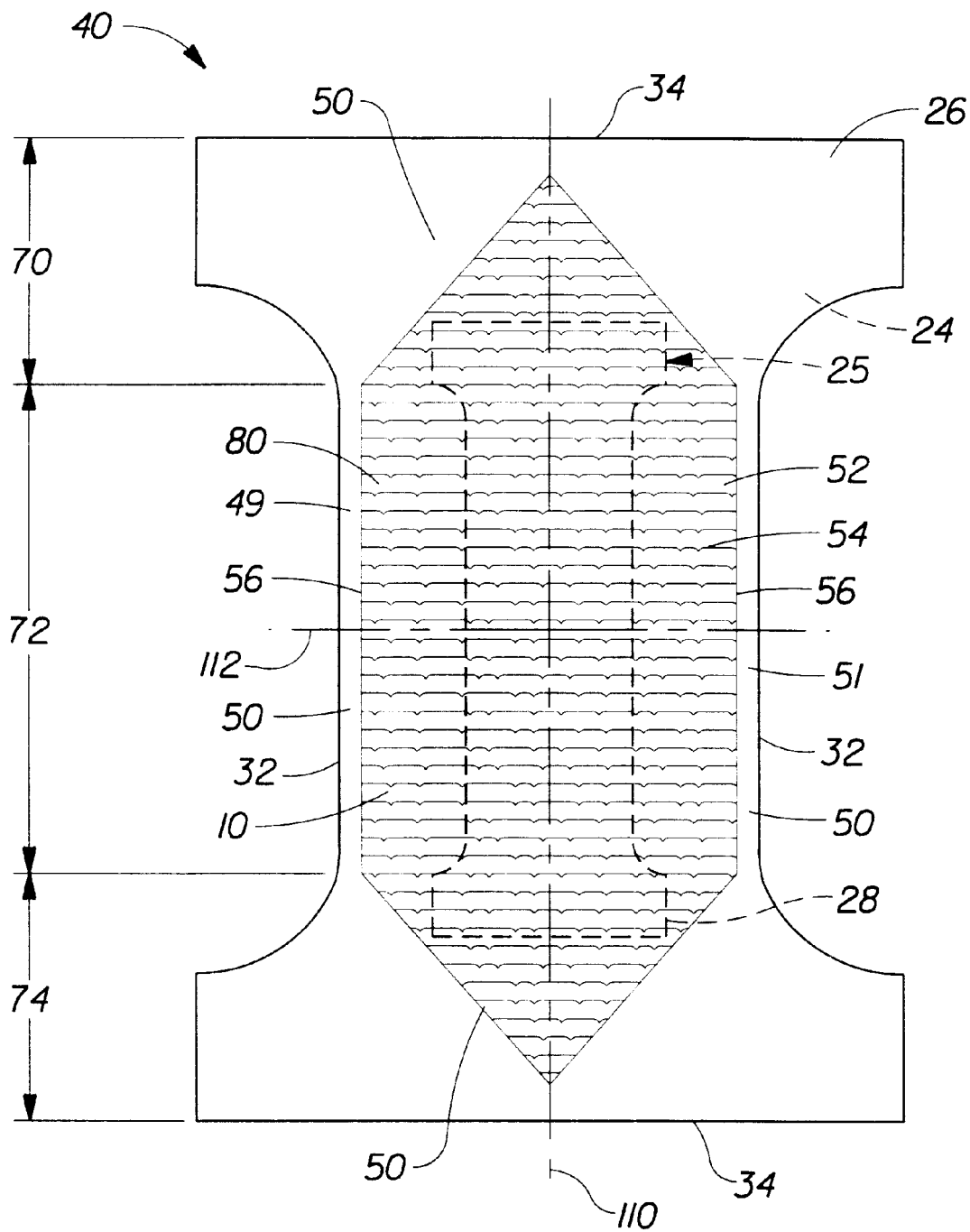
FIG. 15 is a plan view of yet another embodiment of a diaper of the present invention, with the backsheet facing the viewer, shown in a flat, uncontracted configuration.
Figure 16:
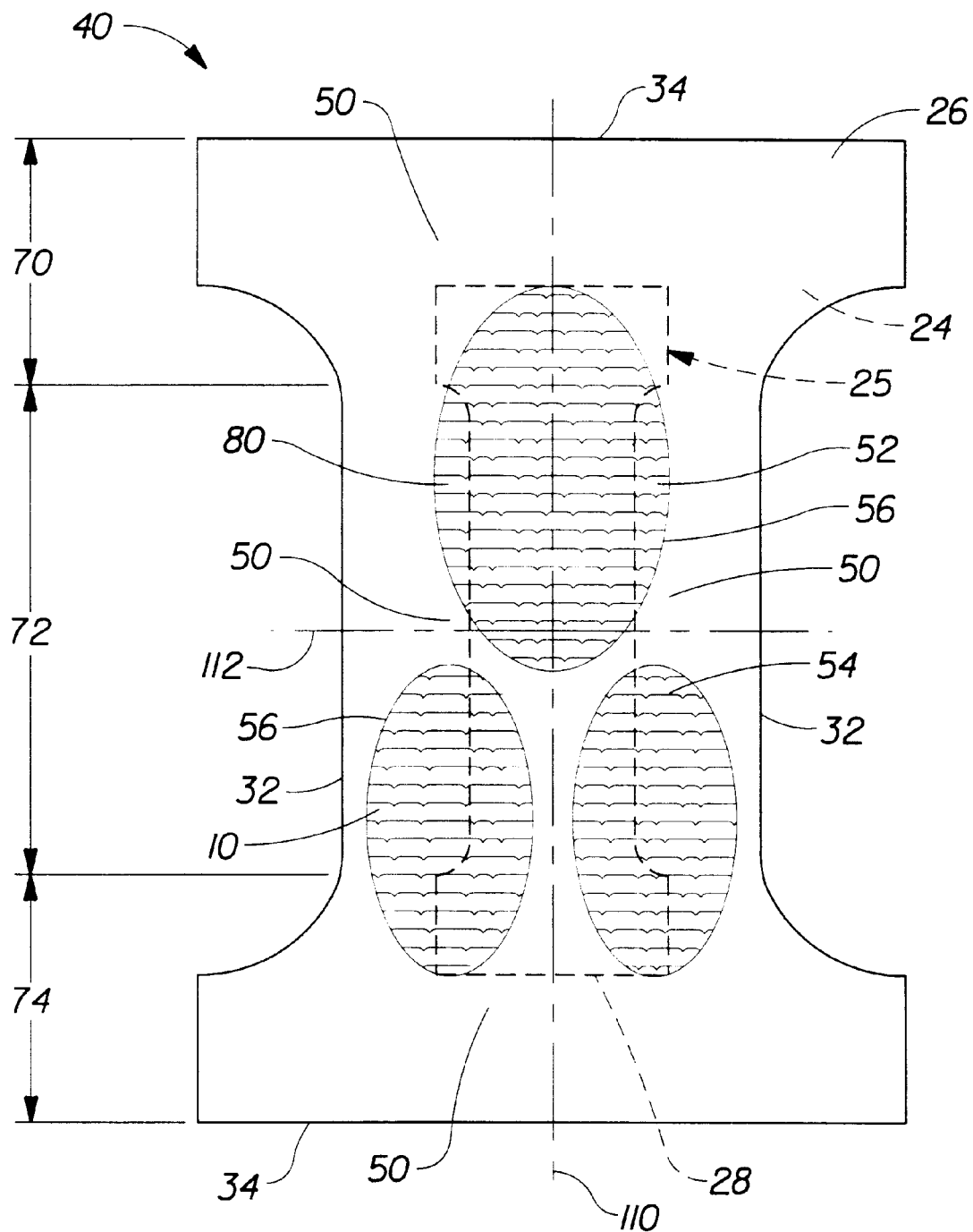
FIG. 16 is a plan view of yet another embodiment of a diaper of the present invention, with the backsheet facing the viewer, shown in a flat, uncontracted configuration.

FIGS. 13–14 show embodiments including at least two pairs of boundary zones 50 surrounding at least a portion of the elongated zone 52. In such embodiments, it is preferred that at least two of the boundary zones 50 are generally parallel to each other. Other preferred nonlimiting embodiments include three or more boundary zones 50 which may completely surround at least a portion of the elongated zone 52. Yet other embodiments include boundary zones 50 which are disposed in generally rectangular, circular, oval, trapezoidal, hexagonal and diamond shaped configurations, some of which are shown in FIGS. 15–17.

The boundary zones 50 may take on any shape and may be of any size. As shown in FIG. 11, the boundary zones 50 may generally comprise the front and rear waist regions 70 and 74 of the diaper 40. In a typical medium sized baby diaper, the boundary zones 50 may be spaced apart from about 1 inch to about 40 inches, more preferably between about 2 inches and about 30 inches, and most preferably between about 3 and about 22 inches. In addition, at least a portion of the boundary zones 50 may take on the shape of narrow strands extending along the longitudinal edges 32 of the diaper 40. In such configurations, one example of which is shown in FIG. 13, the portions of the boundary zones 50 extending along the longitudinal edges 32 of the diaper 40 preferably have generally parallel edges that are between about 1/32 inch and about 1 inch in width. More preferably, the portions of the boundary zones 50 are between about 1/16 inch and about 3/4 inch, and most preferably between about 1/8 inch and about 1/2 inch, in width.

Preferred spacing of the boundary zones 50 from the longitudinal edges of the absorbent core 28 may be, for example, between about 0 inches and about 10 inches, more preferably between about 1/8 inch and about 8 inches. It should be noted that in some embodiments, the spacing between the boundary zones 50 from the longitudinal edges 32 may vary along the length of the longitudinal edges 32 or may vary from one side of the diaper 40 to the other.

In preferred embodiments, the elongated zone 52 may have a surface pathlength which is between about 5% and about 500% greater than the surface pathlength of the boundary zones 50. More preferably, the surface pathlength of the elongated zone 52 is between about 10% and about 250% greater than the surface pathlength of the boundary zones 50, and most preferably the surface pathlength of the elongated zone 52 is between about 20% and about 100% greater than that the surface pathlength of the boundary zones 50.

As shown in FIG. 13, the diaper 40 may comprise a backsheet 26 comprising a formed substrate 80 with an elongated zone 52 having elongation in more than one direction. It should be noted that the number of directions that the elongated zone 52 can be elongated in is unlimited except that at least a portion of the elongated zone 52 must have a surface pathlength that is greater than that of the surface pathlength of the boundary zone 50 along the transition zone 57 when the substrate 80 is in a relaxed condition. Further, the amount of elongation may vary within the elongated zone 52 or multiple elongated zones may exist within a single article. FIG. 14 shows one example of a diaper 40 which has a region of differential incremental stretching 53. As described above, "differential incremental stretching" refers to incremental stretching that provides the particular regions of the substrate with different shape and/or stretch characteristics. The region(s) of differential incremental stretching 53 may provide a pocket for bodily exudates or may provide for improved fit.

The diaper 40 is preferably applied to the wearer by first positioning one of the waist regions, preferably the rear waist region 74, under the wearer's back. The remainder of the diaper 40 is then drawn between the wearer's legs such that the other waist region, preferably the front waist region 70, is positioned across the front of the wearer. The diaperer then wraps the sides or side panels of the diaper 40 around the waist of the wearer and fastens the rear waist region 74 to the front waist region 70 on each side of the wearer to form a waist closure on each side of the wearer.

While particular embodiments of the present invention have been illustrated and described, it would be obvious to those skilled in the art that various other changes and modifications can be made without departing from the spirit and scope of the present invention. It is therefore intended to cover in the appended claims all such changes and modifications that are within the scope of this invention.

What is claimed is:

1. A macroscopically three-dimensional formed substrate comprising:
   (a) a first boundary zone having a first surface pathlength and a second boundary zone having a second surface pathlength, said first and said second surface pathlengths measured when said formed substrate is in a relaxed condition; and
   (b) an elongated zone located at least partially between said first boundary zone and said second boundary zone, said elongated zone comprising incrementally stretched regions which result in said elongated zone being elongated in a first direction of elongation, said elongated zone having a third surface pathlength measured generally parallel to said first direction of elongation when said formed substrate is in said relaxed condition, said third surface pathlength being greater than either said first pathlength or said second pathlength such that said substrate takes on a macroscopic three-dimensional configuration when said substrate is in said relaxed condition.

2. The macroscopically three-dimensional formed substrate of claim 1 wherein said third surface pathlength is greater than both said first surface pathlength and said second surface pathlength.

3. The macroscopically three-dimensional formed substrate of claim 1 wherein said elongated zone of said formed substrate comprises regions of differential incremental stretching.

4. The macroscopically three-dimensional formed substrate of claim 1 wherein said first and said second boundary zones of said formed substrate are elastomeric.

5. The macroscopically three-dimensional formed substrate of claim 1 comprising at least three boundary zones, said first boundary zone, said second boundary zone and a third boundary zone.

6. The macroscopically three-dimensional formed substrate of claim 5 wherein said boundary zones completely surround at least a portion of said elongated zone.

7. The macroscopically three-dimensional formed substrate of claim 5 wherein said elongated zone has regions of incremental stretching which elongate said elongated zone in said first direction of elongation and at least one other direction of elongation.

8. An absorbent article having a pair of opposed longitudinal edges,
   an absorbent assembly having an inner facing side and an outer facing side;
   a backsheet joined with said outer facing side of said absorbent assembly, said backsheet including a formed substrate comprising:
   (a) a first boundary zone having a first surface pathlength and a second boundary zone having a second surface pathlength, said first and said second surface pathlengths measured when said formed substrate is in a relaxed condition; and (b) an elongated zone located at least partially between said first boundary zone and said second boundary zone, said elongated zone comprising incrementally stretched regions which result in said elongated zone being elongated in a first direction of elongation, said elongated zone having a third surface pathlength measured generally parallel to said first direction of elongation when said formed substrate is in said relaxed condition, said third surface pathlength being greater than either said first pathlength or said second pathlength such that said backsheet takes on a macroscopic three-dimensional configuration when said backsheet is in said relaxed condition.

9. The absorbent article of claim 8 wherein said first boundary zone and said second boundary zone extend generally parallel to said longitudinal edges, and said first direction of elongation is generally parallel to said longitudinal edges.

10. The absorbent article of claim 8 wherein said absorbent assembly comprises a topsheet, said backsheet joined with said topsheet, and an absorbent core positioned between said topsheet and said backsheet, said topsheet comprising at least a portion of said inner facing side of said absorbent assembly, and said backsheet being positioned adjacent said outer facing side of said absorbent assembly.

11. The absorbent article of claim 10 wherein said topsheet includes a second formed substrate comprising a first boundary zone and a second boundary zone each extending generally parallel to said longitudinal edges, said first boundary zone having a first surface pathlength and said second boundary zone having a second surface pathlength, both said first and said second surface pathlength measured when said second formed substrate is in a relaxed condition; and an elongated zone located between said boundary zones, said elongated zone comprising incrementally stretched regions which result in said elongated zone being elongated in a first direction, said elongated zone having a third surface pathlength measured generally parallel to said first direction of elongation when said second formed substrate is in said relaxed condition, said third surface pathlength being greater than either said first pathlength or said second pathlength such that said topsheet takes on a macroscopic three-dimensional configuration when said topsheet is in said relaxed condition.

12. The absorbent article of claim 8 wherein said first boundary zone and said second boundary zone extend generally perpendicular to said longitudinal edges and said first direction of elongation is generally perpendicular to said longitudinal edges.

13. The absorbent article of claim 12 wherein said absorbent assembly comprises a topsheet, said backsheet joined with said topsheet, and an absorbent core positioned between said topsheet and said backsheet, said topsheet comprising at least a portion of said inner facing side of said absorbent assembly, and said backsheet being positioned adjacent said outer facing side of said absorbent assembly.

14. The absorbent article of claim 13 wherein said topsheet includes a second formed substrate comprising a first boundary zone and a second boundary zone each extending generally perpendicular to said longitudinal edges, said first boundary zone having a first surface pathlength and said second boundary zone having a second surface pathlength, both said first and said second surface pathlength measured when said second formed substrate is in a relaxed condition; and an elongated zone located between said boundary zones, said elongated zone comprising incrementally stretched regions which result in said elongated zone being elongated in a first direction, said elongated zone having a third surface pathlength measured generally parallel to said first direction of elongation when said second formed substrate is in said relaxed condition, said third surface pathlength being greater than either said first pathlength or said second pathlength such that said topsheet takes on a macroscopic three-dimensional configuration when said topsheet is in said relaxed condition.

15. The absorbent article of claim 14 wherein said elongated zone of said formed substrate comprises regions of differential incremental stretching.

16. The absorbent article of claim 15 wherein said first and said second boundary zones of said formed substrate are elastomeric.

17. A sanitary napkin having a pair of opposed longitudinal edges,
a topsheet; a backsheet joined with said topsheet; and an absorbent assembly positioned between said topsheet and said backsheet, said absorbent assembly having an inner facing side and an outer facing side, said topsheet being positioned adjacent said inner facing side of said absorbent assembly and said backsheet being positioned adjacent said outer facing side of said absorbent assembly;
said backsheet including a formed substrate comprising:
(a) a first boundary zone extending generally parallel to said longitudinal edges, one of said boundary zones having a first surface pathlength and a second boundary zone having a second surface pathlength, said first and said second said boundary zones extending generally parallel to said longitudinal edges, said first and said second surface pathlengths measured when said formed substrate is in a relaxed condition, each said boundary zone having a width between about 0.1 cm and about 3.0 cm, said boundary zones being spaced apart between about 1.0 cm and about 30.0 cm; and
(b) an elongated zone located at least partially between said first boundary zone and said second boundary zone, said elongated zone comprising incrementally stretched regions which result in said elongated zone being elongated in a first direction of elongation, said elongated zone having a third surface pathlength measured generally parallel to said first direction of elongation when said formed substrate is in said relaxed condition, said third surface pathlength being greater than either said first pathlength or said second pathlength such that said backsheet takes on a macroscopic three-dimensional configuration when said backsheet is in said relaxed condition.

18. The absorbent article of claim 17 wherein said third surface pathlength is greater than both said first surface pathlength and said second surface pathlength.

19. The sanitary napkin of claim 17 wherein said width of said boundary zones is between about 0.2 cm and about 1.5 cm.

20. The sanitary napkin of claim 17 wherein said boundary zones are spaced apart between about 2.0 cm and about 15.0 cm.

21. The sanitary napkin of claim 17 wherein said boundary zones are spaced apart between about 4.0 cm and about 10.0 cm.

22. The absorbent article of claim 17 wherein said topsheet includes a second formed substrate comprising a first boundary zone and a second boundary zone each extending generally parallel to said longitudinal edges, said first boundary zone having a first surface pathlength and said second boundary zone having a second surface pathlength, both said first and said second surface pathlength measured when said second formed substrate is in a relaxed condition; and an elongated zone located between said boundary zones, said elongated zone comprising incrementally stretched regions which result in said elongated zone being elongated in a first direction, said elongated zone having a third surface pathlength measured generally parallel to said first direction of elongation when said second formed substrate is in said relaxed condition, said third surface pathlength being greater than either said first pathlength or said second pathlength such that said topsheet takes on a macroscopic three-dimensional configuration when said topsheet is in said relaxed condition.

23. The absorbent article of claim 17 wherein said elongated zone of said formed substrate comprises regions of differential incremental stretching.

24. The absorbent article of claim 17 wherein said boundary zones are elastomeric.

* * * * *